(12) United States Patent
Reiter et al.

(10) Patent No.: US 7,453,354 B2
(45) Date of Patent: Nov. 18, 2008

(54) DEVICE ARRANGED FOR CARRYING OUT A BIOELECTRICAL INTERACTION WITH AN INDIVIDUAL AND A METHOD FOR ON-DEMAND LEAD-OFF DETECTION

(75) Inventors: Harald Reiter, Aachen (DE); Andras Montvay, Stuttgart (DE); Josef Lauter, Geilenkirchen (DE); Olaf Such, Aachen (DE); Ralf Schmidt, Aachen (DE)

(73) Assignee: Koninklijke Philips Electronics, N.V., Eindhoven (NL)

( * ) Notice: Subject to any disclaimer, the term of this patent is extended or adjusted under 35 U.S.C. 154(b) by 158 days.

(21) Appl. No.: 10/574,892

(22) PCT Filed: Oct. 7, 2004

(86) PCT No.: PCT/IB2004/052007

§ 371 (c)(1),
(2), (4) Date: Apr. 4, 2006

(87) PCT Pub. No.: WO2005/037099

PCT Pub. Date: Apr. 28, 2005

(65) Prior Publication Data

US 2007/0018809 A1    Jan. 25, 2007

(30) Foreign Application Priority Data

Oct. 17, 2003    (EP)    ................... 03103845

(51) Int. Cl.
*G08B 1/08*    (2006.01)
(52) U.S. Cl. .................... 340/539.12; 600/372; 600/509
(58) Field of Classification Search ............ 340/539.12, 340/286.07, 573.1, 539.14, 539.17; 600/301, 600/306, 372, 382, 384, 509, 523, 481
See application file for complete search history.

(56) References Cited

U.S. PATENT DOCUMENTS 3,972,320 A * 8/1976 Kalman ...................... 600/519

(Continued)

*Primary Examiner*—Brent Swarthout
(74) *Attorney, Agent, or Firm*—Tony Piotrowski

(57) ABSTRACT

A device to carry out a bioelectrical interaction with an individual by means of electrodes 29, 29a whereby an on-demand verification of the integrity of the electrical contact of the electrodes is implemented. The device 20 comprises a control unit 22 arranged to determine an occurrence of the predefined event related to a quality of a measured signal. In case the predetermined event is detected, the control unit 22 actuates the testing means 24. The testing means is arranged to generate the test signals, I1, I2 and to apply them via a coupling circuit 23, 23a to the electrodes. In case it is desired that cumulative information about the contact integrity is obtained, is it sufficient to apply a single test signal per electrode. In case it is required to determine which of the electrodes has lost its contact, a sequence of test signals is generated by the sequencer 24b. The response signal from the electrodes 29, 29a is forwarded to the input filter 26, which is preferably also used for a normal signal analysis. The signal from the input filter 26 is directed via the input impedance 25, 25a to the input amplifier 28. The amplified response signal is forwarded to the signal processing means 30 which is arranged to analyze the response signal. Preferably, an amplitude analysis is done. The signal from the signal processing means 30 is supplied to the analog-to-digital converter (ADC) 32 after which a digital processing of the response signal is carried out by means of a further processing unit 34. In case the further processing unit 34 determines that the integrity of the contact is below the allowable level, the lead-off indicator 36 is actuated.

9 Claims, 4 Drawing Sheets

U.S. PATENT DOCUMENTS

| | | |
|---|---|---|
| 4,417,590 A | 11/1983 | Smith et al. |
| 4,498,479 A * | 2/1985 | Martio et al. ............... 600/372 |
| 5,003,975 A | 4/1991 | Hafelfinger et al. |
| 5,692,215 A * | 11/1997 | Kutzik et al. .................. 710/18 |
| 5,729,203 A * | 3/1998 | Oka et al. ................ 340/573.1 |
| 6,160,478 A * | 12/2000 | Jacobsen et al. ....... 340/539.12 |
| 6,287,252 B1 * | 9/2001 | Lugo .......................... 600/300 |
| 6,387,048 B1 * | 5/2002 | Schulman et al. ........... 600/300 |
| 6,980,112 B2 * | 12/2005 | Nee ........................ 340/573.1 |
| 2003/0105403 A1 * | 6/2003 | Istvan et al. ................. 600/509 |
| 2004/0225210 A1 * | 11/2004 | Brosovich et al. ........... 600/372 |

* cited by examiner

DEVICE ARRANGED FOR CARRYING OUT A BIOELECTRICAL INTERACTION WITH AN INDIVIDUAL AND A METHOD FOR ON-DEMAND LEAD-OFF DETECTION

The invention relates to a device arranged for carrying-out a bioelectrical interaction with an individual, said device comprising:
sensing means comprising a plurality of electrodes arranged to measure a first electrical signal when brought into contact with an individual's skin;
testing means arranged to deliver a second electrical signal to a corresponding input of said electrodes, said electrodes being further arranged to generate a response signal upon receipt of the second electrical signal.

The invention further relates to a method for on-demand verification of the integrity of an electrical contact of an electrode to a body part of an individual, wherein said electrode is part of a device arranged to carry-out a bio-electrical interaction with the individual.

A device as set forth in the opening paragraph is known from U.S. Pat. No. 5,792,063. The known device is arranged for measuring an electrocardiogram of an individual by means of a set of measuring electrodes attached to the individual's skin. The known device further comprises a neutral electrode attached to the body of the individual, which is thus electrically connected to the measuring electrodes by the body impedance. The known device further comprises testing means arranged to deliver a test signal to the neutral electrode thus inducing a response signal in the measuring electrodes. By continuously applying the test signal and by monitoring the response signal of the measuring electrodes, the integrity of the contact of the measuring electrodes to the individual's body is continuously verified.

It is a disadvantage of the known device that an additional neutral electrode is needed for purposes of a lead-off monitoring. The integrity of the contact of the measuring electrodes is verified indirectly by inducing a test signal into the measuring circuit by means of the neutral electrode. In case the contact integrity of the neutral electrode is deteriorated, the system will give rise to erroneous results. Further, the known device is arranged for a continuous monitoring of the contact integrity. For battery-powered portable devices arranged to carry out a bioelectrical interaction, the system up-time will be reduced substantially with the known set-up thus limiting an applicability of the device as a whole.

It is an object of the invention to provide a device as is set forth in the opening paragraph where lead-off detection is carried out accurately and imposes a minimal power consumption of the system.

To this end the device according to the invention comprises:
a control unit arranged to analyze the first electrical signal and to actuate the testing means upon an occurrence of a predetermined event in the first electrical signal;
lead-off detection means arranged to verify an integrity of the contact of said electrodes by analyzing the response signal and detecting a parameter related to said integrity.

The technical measure of the invention is based on the insight that it is advantageous to verify the integrity of the contact only in case a predetermined event in the measured signal is detected. An example of the predetermined event is a deterioration of the signal-to-noise ratio of the measured signal or any other suitable quantitative parameter. Only in case the predetermined event is detected, the control unit of the device according to the invention actuates the testing means which deliver the second electrical signal to the corresponding input of the electrodes of the sensing means. The corresponding response signal is then analyzed by the lead-off detection means. Preferably, the lead-off detection means comprises a comparator arranged to compare an amplitude of the response signal with a reference value. In this case the amplitude serves as the parameter related to the integrity of the contact. Alternatively, the lead-off detection means can comprise a digital circuitry arranged to carry out a digital analysis of the response signal. Suitable hardware for these purposes is known per se in the art of signal processing. According to the technical measure of the invention a smart device is provided where the contact integrity is being verified directly and on demand thus improving the up-time of the device and its reliability. It must be noted that no neutral electrode is needed in the device according to the invention thus yielding a simple and reliable system which also improves a wearing comfort of the individual. In the art of devices arranged for carrying out a bioelectrical interaction it is understood that a wearing comfort is usually one of the critical parameters determining a consumer's preference. By avoiding an additional electrode, the skin irritation of the individual can be moderated thus increasing a possible wearing time.

In an embodiment of the device according to the invention the testing means comprises a signal generator arranged to generate the second electrical signal in substantially the same bandwidth as the first electrical signal. In the art of monitoring an alternative signal, like an electrocardiogram, electroencephalogram, respiration rate or any other source of alternating signal, it is particularly advantageous to carry out an in-band testing. In this way the same hardware can be used for testing purposes as for monitoring purposes, yielding a simple device with minimum additional manufacturing costs and a minimum increase in the device dimensions. The latter is of particular importance for portable monitoring devices arranged for continuous operation.

In a further embodiment of the device according to the invention the testing means further comprises a sequencer arranged to deliver a sequence of variable second electrical signals to each input of said electrodes in order to determine the integrity of the contact of each electrode within said plurality of electrodes. In case the sensing means of the device comprises a substantial number of electrodes, it is found to be particularly advantageous to provide a possibility of an automatic determination which of the electrodes has a deteriorated contact integrity. For this purpose a sequence of different test signals is generated by the testing means. An example of suitable test signals in shown in Table 1.

TABLE 1

Possible setting for two test signals to detect the contact integrity.

| Input 1 | NORM | INV | NORM | OFF | NORM |
| Input 2 | NORM | NORM | INV | NORM | OFF | where
NORM indicates a normal test signal, for example a square wave 10 Hz, 3 Volts.
INV indicates inverted Norm signal;
OFF means no signal generated.

Although the Table 1 shows an example of a two-electrode set-up, this method can be used for a greater number of electrodes. By changing and/or varying the test signals indicated by Input 1, Input 2 in Table 1, it is possible to detect whether the first electrode or the second electrode or both have sufficient contact to the body of the individual. The analysis of the response signal is preferably done by signal processing in the system processor.

In a still further embodiment of the device according to the invention the device further comprises a lead-off indication means, said lead-off detection means being actuable by the lead-off detection means upon a detection of said parameter. It is found to be advantageous to signal the deteriorated contact integrity to the individual and/or to a caregiver. This feature is of particular advantage in case the bioelectrical interaction comprises a delivery of an electrical discharge, in the field of electrostimulation. An example of an envisaged electrostimulation is an application of a defibrillating shock to a heart patient, or an application of a myostimulating signal for other therapeutic purposes.

These and other aspects of the invention will be further discussed with reference to figures.

Figure 1:
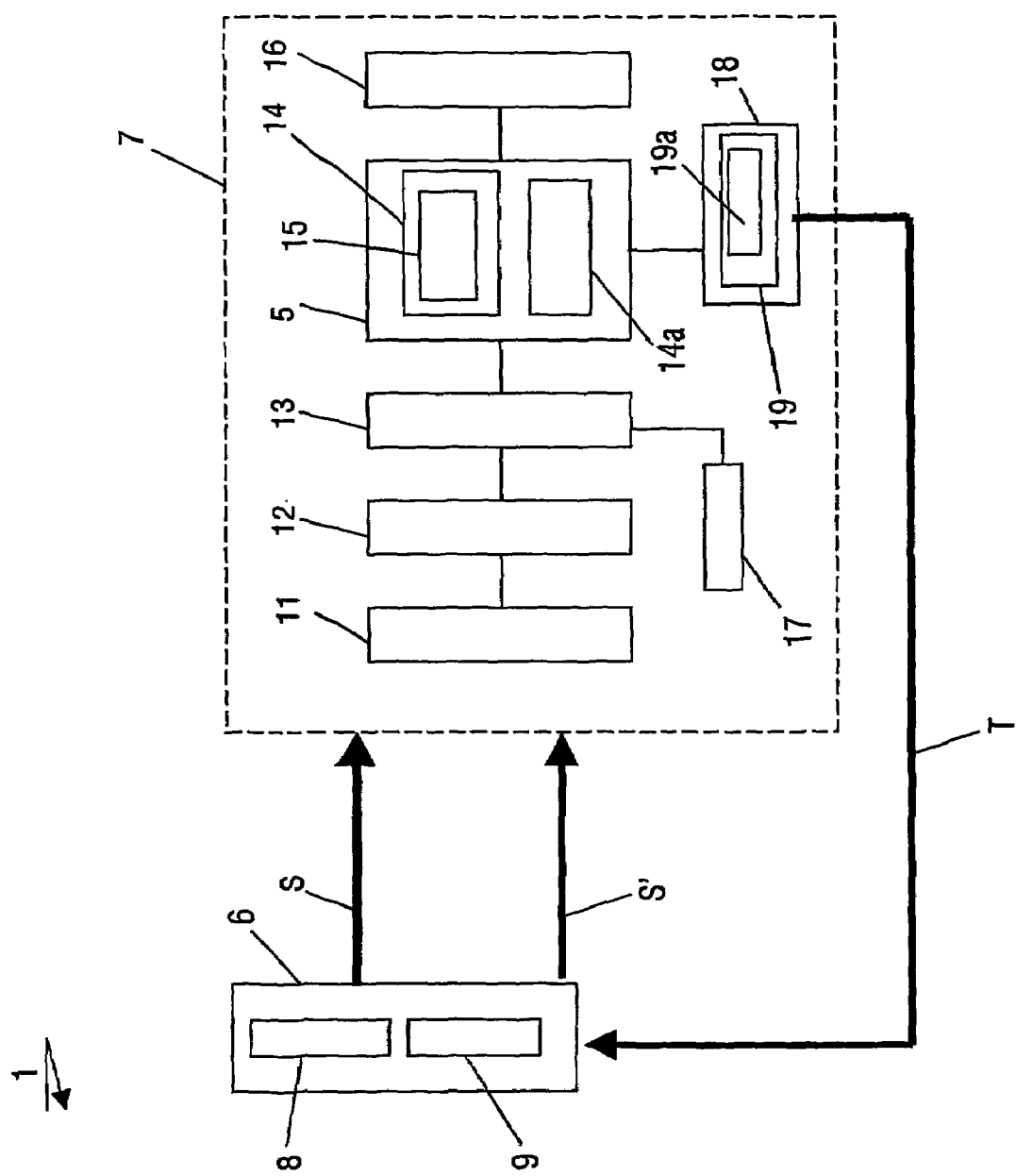
FIG. 1 shows a schematic view of an embodiment of front-end electronics of the device according to the invention.

FIG. 1 shows a schematic view of an embodiment of front-end electronics of the device according to the invention. The device 1 comprises the sensing means 6 provided with two electrodes 8, 9 arranged to measure a first electrical signal S when brought into contact with the individual's skin. The signal S, from the electrodes is supplied to the front-end electronics 7 of the device 1. The front-end electronics 7 is arranged to analyse said signal in order to derive a suitable health-related parameter which is further used by the device 1 for monitoring and/or therapeutic purposes. The front-end electronics 7 comprises an input amplifier and analogue processing circuit 11, an ADC unit 12, a μ-processor 13 and a control unit 5. The control unit 5 comprises a sensor signal interpretation unit 14 provided with event extraction means 15. The device 1 further comprises testing means 18 actuable by the detection means 5 in case the predetermined event is detected. The testing means 18 is arranged to generate a test signal by means of a generator 19, said test signal being preferably in-band with the measured signal. The generator 19 is further arranged to apply the test signal T to the corresponding input of the electrodes 8,9. During an application of the test signal T the electrodes 8,9 do not measure the first electrical signal and produce a response signal S', which is supplied to the front-end electronics 7 in the same way as the measuring signal S. It must be noted that any measurable influence of the test signal induced by the electrodes is referred to as the response signal S'. At the front-end electronics 7 the response signal S' is processed and analyzed by the control unit 5. In case the control unit 5 determines that the contact of the electrodes with the individual's skin is below acceptable value, the lead-off indicator 16 is actuated signalling about a detachment of the electrodes 8, 9.

The device 1 operates as follows: when the corresponding contact surfaces of the electrodes are put in contact with the individual's skin, the electrodes 8, 9 provide a corresponding input signal S to the front-end electronics 7. The front-end electronics 7 provides means for receiving the signals from the sensing means, performs suited analog processing by means of the analog processing circuit 11. The processed raw data is converted into a digital format by means of the ADC 12 and is forwarded to the control unit 5, where a suitable health-related parameter of the individual is being analysed. For example, for cardiac applications the control unit 5 can comprise a QRS-detector known per se to determine R-R peak intervals in heart cycles. The control unit 5 comprises a signal interpretation unit 14 arranged to derive a predetermined event 15. For example, for cardiac applications said feature can be a frequency, an amplitude or a signal-to-noise ratio of the signal. Preferably, a reference value of the predetermined event is stored in a look-up table (not shown) of the memory unit 17. Additionally, the system can be arranged as a self-learning system, where a threshold value for the predetermined event is being adjusted and stored in the look-up table in case a pre-stored reference value does not correspond to a deteriorated contact integrity for a particular user. This feature is particularly important for monitoring exercising people. The control unit 5 is further arranged to provide a trigger signal to the test means 18 in case the predetermined event is detected. The test means 18 generates a test signal which is then directed to the electrodes 8,9. The control unit 5 further comprises a lead-off detection means 14a arranged to verify an integrity of the contact of said electrodes by analyzing the response signal S' and detecting a parameter related to said integrity. An example of a suitable parameter is a threshold value of the amplitude of the response signal S'. In case the contact integrity is below a predetermined allowable level, the lead-off indicator means 16 is actuated by the lead-off detection means 14a.

Figure 2:
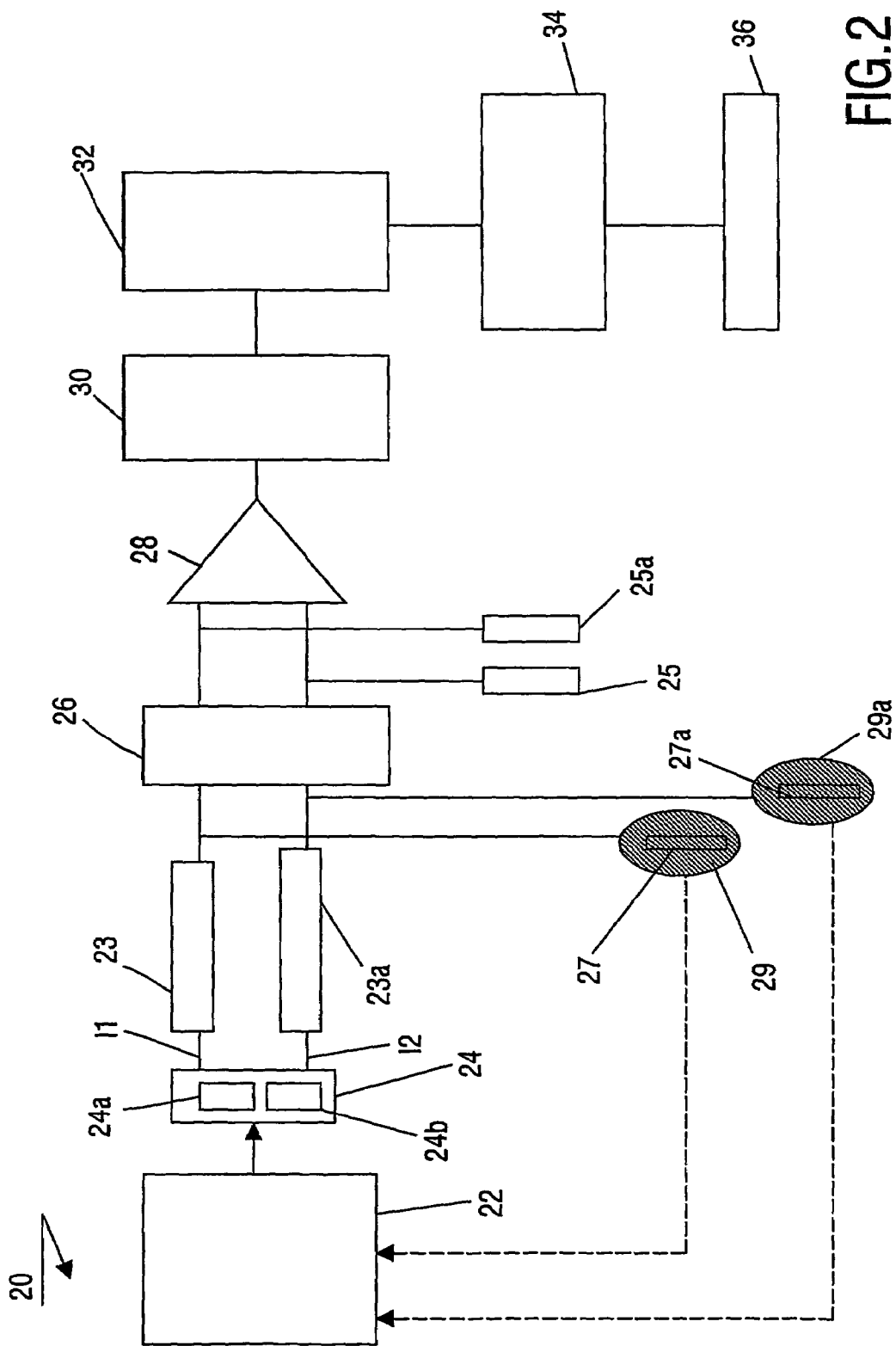
FIG. 2 shows a schematic view of an embodiment of a two-lead ECG circuit.

FIG. 2 shows a schematic view of an embodiment of a two-lead ECG circuit. In order to carry out an on-demand verification of the integrity of the electrical contact of the electrodes 29, 29a, the device 20 comprises a control unit 22 arranged to determine an occurrence of the predefined event. For example, in case of a cardiac monitoring, the predetermined event can be assigned to a certain value of an amplitude of the signal, a signal-to-noise ratio or to any other suitable signal characteristic. In case the predetermined event is detected, the control unit 22 actuates the test means 24. The test means is arranged to generate the test signals, I1, I2 and to apply them via a coupling circuit 23, 23a to the electrodes, schematically represented by 29, 29a A typical value of the impedance of the coupling circuit is in the order of 100 MOhm. The formation of the test signal is preferably done by means of a generator 24a in accordance with Table 1. In case it is desired that a cumulative information about the contact integrity is obtained, it is sufficient to apply a single test signal per electrode. In case it is required to determine which of the electrodes has lost its contact, a set of the test signals in accordance with Table 1 is generated by a suitable sequencer 24b. The patient's skin is electrically represented by the corresponding impedance 27, 27a, which lies in the order of 1 MOhm for dry electrodes and in the order of 100kOhm for moist electrodes. The response signal from the electrodes 29, 29a is forwarded to the input filter 26, which is preferably also used for a normal signal analysis. The signal from the input filter 26 is directed via the input impedance 25, 25a to the input amplifier 28. The amplified response signal is forwarded to the signal processing means 30 which is arranged to analyze the response signal. Preferably, an amplitude analysis is done. The signal from the signal processing means 30 is supplied to the analog-to-digital converter (ADC) 32 after which a digital processing of the response signal is carried out by means of a further processing unit 34. In case the further processing unit 34 determines that the integrity of the contact is below the allowable level, the lead-off indicator 36 is actuated.

Figure 3:
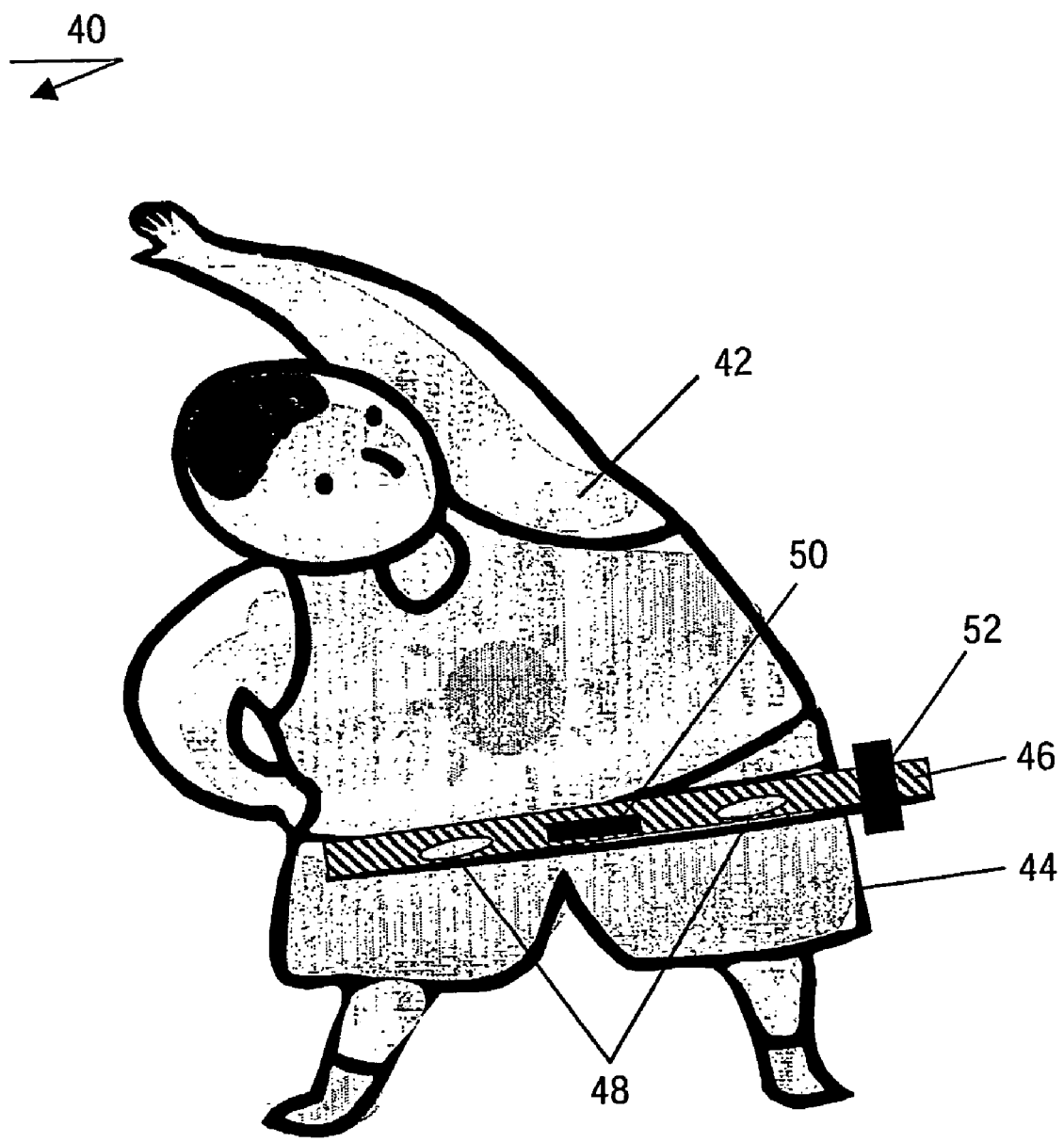
FIG. 3 shows a schematic view of an embodiment of a device arranged for monitoring a physiological condition of the individual.

FIG. 3 shows a schematic view of an embodiment of a device arranged for monitoring a physiological condition of the individual. In this example the device 40 is arranged as a body-wear comprising a wearable article of clothing 44 provided with a carrier 46 on which a set of electrodes 48 is mounted, said electrodes being arranged to monitor the cardiac activity of the individual. It must be noted that this embodiment is used for illustration purposes only and cannot be used to limit the scope of the invention. The device 40 further comprises a control unit 52 arranged to analyze the signals from the electrodes 48 and to determine an occurrence of a predefined event in accordance with FIG. 1. In case it is found that the predetermined event has occurred, for example a signal-to-noise ratio of the measured signal has fallen, the control unit 52 actuates the test means 50 which is arranged to deliver a test signal to the electrodes. Suitable examples of the test signals can be found in Table 1. The response signals generated by the electrodes are analyzed by the control unit 52 in order to determine a parameter related to the integrity of the contact of the electrodes. In case such a parameter is determined and it is found that the contact integrity is below allowable level, the lead-off indicator (not shown) is actuated to alarm the individual and/or a carer about a detachment of the electrodes.

Figure 4:
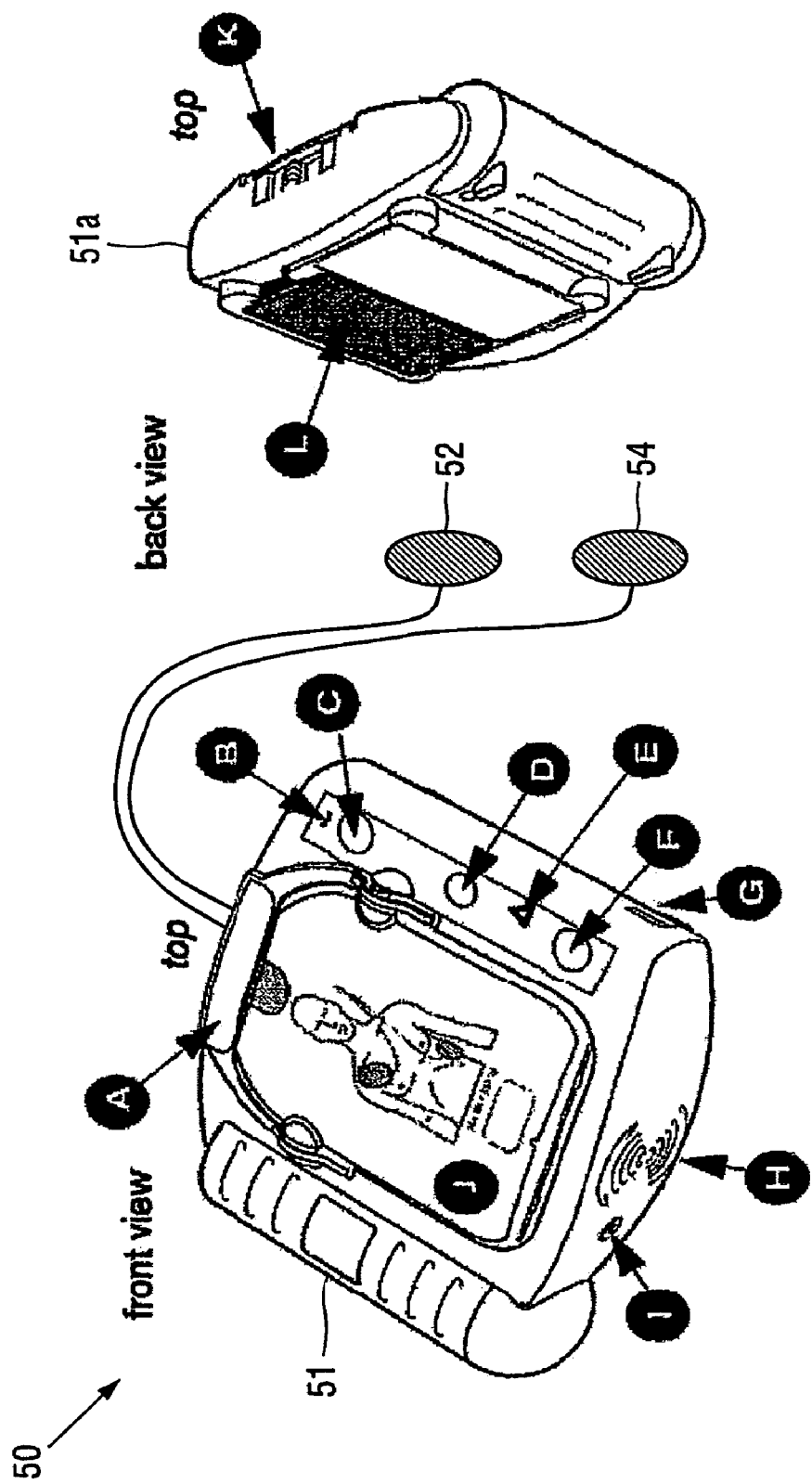
FIG. 4 shows a schematic view of an embodiment of a device arranged for electrostimulation of a body part of the individual.

FIG. 4 shows a schematic view of an embodiment of a device arranged for electrostimulation of a body part of the individual. A plurality of units are suitable for this purpose including myostimulators of various types and automatic external defibrillators. In the embodiment of FIG. 4 an automatic external defibrillator (AED) is shown. The AED 50 comprises a control unit, shown in a front view 51 and a rear view 51a, said control unit being arranged to interact with the external leads 52 and 54 by means of which first an electrocardiogram of a person suffering from a cardiac insufficiency is measured. The control unit 51 comprises a handle A, an On/Off button C and user panel J, whereon procedural steps and guiding instructions are projected after a start-up of the AED. It is also indicated where the electrodes 52 and 54 are to be placed on the person. A light indicator B provides an additional feedback to the operator. The control unit 51 further comprises additional informative indicators D,E. A button F is a shock-delivery button and G is an infrared communications port. The control unit 51 further comprises a battery L and a smart pads cartridge latch. In case the AED is in a standby mode, the light indicator B is blinking, for an in-use state the light indicator B provides a constant light. In case the control unit 51 determines that a condition of the person is shockable, a lead-off detection is carried out in order to avoid unnecessary shocking in case the signal quality has deteriorated due to a detachment of an electrode. For this purpose the AED unit 50 is arranged with testing means (not shown) arranged to deliver a test signal to the electrodes. The response signal from the electrodes is analyzed by the same circuitry as is used for the ECG analysis. In case it is determined that any of the electrodes is detached, a visual alarm I and/or audio alarm H are actuated in order to warn a bystander that a previous acquisition of the ECG may be incorrect. According to the technical measure of the invention the AED is supplied with a simple and reliable automatic lead-off detection means which ensures a reliable operation of the system as a whole.

Although the invention has been described with reference to preferred embodiments thereof, it is to be understood that these are not limitative examples. Thus, various modifications may become apparent to those skilled in the art, without departing from the scope of the invention, as defined by the claims. The invention can be implemented by means of both hardware and software, and several 'means' may be presented by the same item in hardware. Any reference characters do not limit the scope of claims.

The invention claimed is:

1. A device arranged for carrying-out a bioelectrical interaction with an individual through electrodes and detecting undesired contact of an electrode with the individual, said device comprising:
   a plurality of electrodes arranged to receive a physiological electrical signal when brought into contact with an individual's skin;
   testing means arranged to deliver a second electrical signal to an input of the electrodes, said electrodes being further arranged to generate a response signal upon receipt of the second electrical signal;
   control unit arranged to analyze the first electrical signal and to actuate the testing means upon an occurrence of a predetermined event in the first electrical signal; and
   lead-off detection means arranged to verify an integrity of the contact of said electrodes by analyzing the response signal and detecting a parameter related to said integrity.

2. A device according to claim 1, wherein the testing means comprises a signal generator arranged to generate the second electrical signal in substantially the same bandwidth as the first electrical signal.

3. A device according to claim 2, wherein the test means further comprises a sequencer arranged to deliver a sequence of variable second electrical signals to each input of said electrodes in order to determine the integrity of the contact of each electrode within said plurality of electrodes.

4. A device according to claim 1, wherein the device further comprises lead-off indication means, said lead-off indication means being actuable by the lead-off detection means upon a detection of said parameter.

5. A device according to claim 1, wherein said bioelectrical interaction comprises monitoring of a physiological condition of the individual.

6. A device according to claim 1, wherein said bioelectrical interaction comprises electro-stimulation of a body part of the individual.

7. A method for on-demand verification of the integrity of an electrical contact of an electrode to a body part of an individual, wherein said electrode is part of a device arranged to carry-out a bio-electrical interaction with the individual, said method comprising the following steps:
   measuring a first physiological electrical signal by means of the electrode;
   analyzing the first physiological electrical signal for occurrence of a predetermined event;
   generating a second electrical signal upon detection of the predetermined event;
   generating a response signal by applying the second electrical signal to an input of the electrode; and
   analyzing the response signal for detecting a parameter related to said integrity.

8. A method according to claim 7, wherein the second electrical signal is generated in substantially the same bandwidth as the first electrical signal.

9. A method according to claim 8, wherein generating a response signal further comprises:
   applying a sequence of variable second electrical signals to each input of a plurality of electrodes; and wherein analyzing the response signal further comprises:
   processing the resulting sequence of response signals in order to determine the integrity of the contact of each electrode within said plurality of electrodes.

* * * * *